US012789158B2

(12) United States Patent
Goetheer et al.

(10) Patent No.: US 12,789,158 B2
(45) Date of Patent: Nov. 10, 2026

(54) REACTOR AND PROCESS FOR THE HYDROGENATION OF CARBON DIOXIDE

(71) Applicant: Nederlandse Organisatie voor toegepast-natuurwetenschappelijk onderzoek TNO, s-Gravenhage (NL)

(72) Inventors: Earl Lawrence Vincent Goetheer, Mol (BE); Marco Johannes Gerardus Linders, Delfgauw (NL); Juliana Garcia Moretz-Sohn Monteiro, Alphen aan den Rijn (NL); Rajat Bhardwaj, Delft (NL)

(73) Assignee: Nederlandse Organisatie voor toegepast-natuurwetenschappelijk onderzoek TNO, 's-Gravenhage (NL)

( * ) Notice: Subject to any disclaimer, the term of this patent is extended or adjusted under 35 U.S.C. 154(b) by 552 days.

(21) Appl. No.: 18/243,770

(22) Filed: Sep. 8, 2023

(65) Prior Publication Data

US 2024/0024832 A1 Jan. 25, 2024

Related U.S. Application Data

(62) Division of application No. 16/963,545, filed as application No. PCT/NL2019/050046 on Jan. 28, 2019, now abandoned.

(30) Foreign Application Priority Data

Jan. 26, 2018 (EP) .................................... 18153753

(51) Int. Cl.

*B01J 8/00* (2006.01)
*B01J 8/06* (2006.01)

(Continued)

(52) U.S. Cl.

CPC ............... *B01J 8/009* (2013.01); *B01J 8/065* (2013.01); *B01J 8/067* (2013.01); *C07C 29/152* (2013.01);

(Continued)

(58) Field of Classification Search

CPC ....... C07C 29/152; C07C 31/04; C07C 41/01; C07C 43/043; B01J 8/065; B01J 8/009; B01J 8/0221; B01J 2219/24785

See application file for complete search history.

(56) References Cited

U.S. PATENT DOCUMENTS 3,358,750 A 12/1967 Thomas
6,716,355 B1 4/2004 Hanemaaijer et al.

(Continued)

FOREIGN PATENT DOCUMENTS

CA 2186222 A1 10/1995
CA 2414657 A1 6/2004

(Continued)

OTHER PUBLICATIONS

Bos J. "A novel condensation reactor for efficient CO2 to methanol conversion for storage of renewable electric energy—ScienceDirect", (Oct. 15, 2015), URL: https://www.sciencedirect.com/science/article/pii/S1385894714013916?via=ihub, (Jun. 14, 2019), XP055596550.

(Continued)

*Primary Examiner* — Jafar F Parsa
(74) *Attorney, Agent, or Firm* — Banner & Witcoff, Ltd.

(57) ABSTRACT

The present invention is directed to a membrane reactor for the hydrogenation of carbon dioxide, said membrane reactor comprising a reaction compartment (2) comprising a catalyst bed, a permeate compartment (4) and a membrane separat- (Continued)

Figure 1:
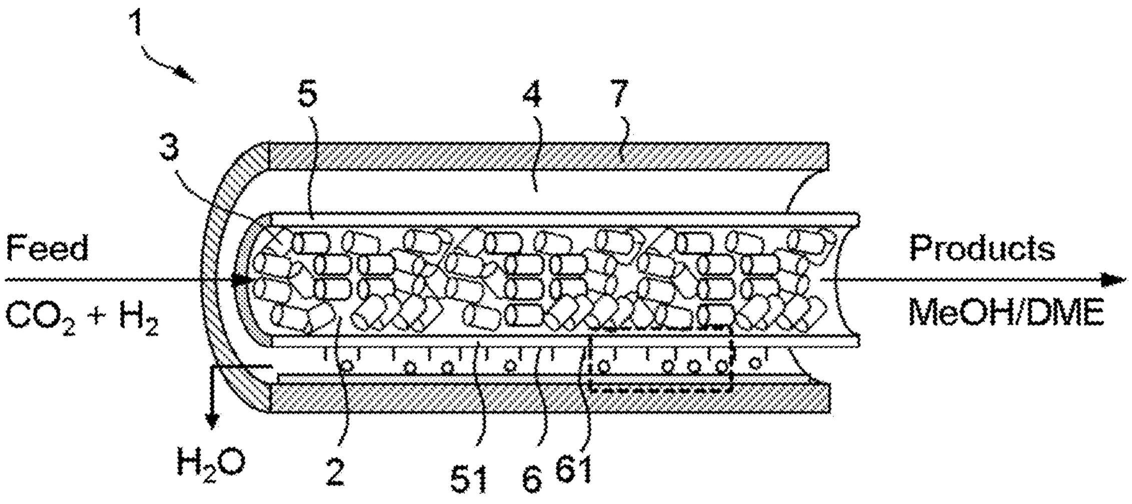

ing the reaction compartment and the permeate compartment, wherein said permeate compartment comprises a condensing surface.

11 Claims, 6 Drawing Sheets

(51) Int. Cl.

| | |
|---|---|
| ***C07C 29/152*** | (2006.01) |
| ***C07C 31/04*** | (2006.01) |
| ***C07C 41/01*** | (2006.01) |
| ***C07C 43/04*** | (2006.01) |

(52) U.S. Cl.

CPC .............. *C07C 31/04* (2013.01); *C07C 41/01* (2013.01); *C07C 43/043* (2013.01); *B01J 2208/00115* (2013.01); *B01J 2208/00168* (2013.01)

(56) References Cited

U.S. PATENT DOCUMENTS

| | | | |
|---|---|---|---|
| 8,425,854 | B1 | 4/2013 | Husain et al. |
| 8,921,619 | B2 | 12/2014 | Harale et al. |
| 2004/0064002 | A1 | 4/2004 | Lee et al. |
| 2009/0170964 | A1 | 7/2009 | Fayyaz Najafi et al. |
| 2011/0266219 | A1 | 11/2011 | Meuleman |
| 2013/0144088 | A1 | 6/2013 | Harale |
| 2016/0318834 | A1 | 11/2016 | Bauer et al. |

FOREIGN PATENT DOCUMENTS

| | | | |
|---|---|---|---|
| CN | 1122796 | A | 5/1996 |
| CN | 1147241 | A | 4/1997 |
| CN | 102584526 | A | 7/2012 |
| CN | 104039435 | A | 9/2014 |
| CN | 105170033 | A | 12/2015 |
| JP | 2018008940 | A | 1/2018 |
| WO | 2013052151 | A1 | 4/2013 |
| WO | 2013144041 | A1 | 10/2013 |
| WO | 2015030578 | A1 | 3/2015 |

OTHER PUBLICATIONS

Diban et al. "Membrane Reactors for in Situ Water Removal: A Review of Applications", Industrial & Engineering Chemistry Research, (Aug. 7, 2013), vol. 52, No. 31, doi:10.1021/ie3029625, ISSN 0888-5885, pp. 10342-10354, XP055596518.

Rohde M P et al. "Fischer-Tropsch synthesis with in situ H"2O removal—Directions of membrane development", Microporous and Mesoporous Materials, 115(2008)123-136, No. 1-2, doi:10.1016/J.MICROMESO.2007.10.052, ISSN 1387-1811, (Feb. 15, 2008), XP023521070.

Haut B et al. "Development and analysis of a multifunctional reactor for equilibrium reactions: benzene hydrogenation and methanol synthesis", Chemical Engineering and Processing, Elsevier Sequoia, Lausanne, CH, vol. 43, No. 8, doi:10.1016/J.CEP.2003.09.006, ISSN 0255-2701, (Dec. 13, 2004), pp. 979-986, (Dec. 13, 2003), XP002733680.

Gallucci F et al. "An experimental study of CO2 hydrogenation into methanol involving a zeolite membrane reactor", Chemical Engineering and Processing, Elsevier Sequoia, Lausanne, CH, vol. 43, doi:10.1016/J.CEP.2003.10.005, ISSN 0255-2701, (Dec. 13, 2003), pp. 1029-1036, (Dec. 13, 2003), XP002546298.

Jadhav et al. "Catalytic carbon dioxide hydrogenation to methanol: A review of recent studies," Chem. Eng. Res. Des., vol. 92, No. 11, pp. 2557-2567, 2014.

Rohde "In-situ H2O Removal via Hydrophilic Membranes During Fischer-Tropsch and Other Fuel Related Synthesis Reactions". KIT Scientific Publ., 2011.

De Falco et al. "Selective membrane application for the industrial one-step DME production process fed by CO2 rich streams: Modeling and simulation," Int. J. Hydrogen Energy, vol. 42, No. 10, pp. 6771-6786, 2017.

Yuan et al. (2013) "Separation of Acetone-Tetrahydrofuran Azeotropic Mixture by Continuous Extractive Distillation," Journal of Chemical Technology & Biotechnology, 88(8), pp. 1523-1528. doi: 10.1002/jctb.3997.

Drioli et al. (2011) "Membrane Engineering in Process Intensification—an Overview," Journal of Membrane Science, 380(1-2), pp. 1-8. doi: 10.1016/j.memsci.2011.06.043.

Wang et al. "Recent advances in membrane distillatin processes: Membrane development, configuration design and application exploring". Journal of Membrane Science, 474 (215) 39-56.

Rohde et al. Membrane Application in Fischer-Tropsch Synthesis to Enhance CO2 Hydrogenation. Ind. Eng. Chem. Res. 2005, 44, 9653-9658. (Year: 2005).

Rohde et al. Fischer-Tropsch Synthesis with In-situ H2O Removal by a New Hydrophilic Membrane—An Experimental and Modelling Study. DGMK/SCI-Conference, "Synthesis Gas Chemistry", Oct. 4-6, 2006, Dresden, Germany. (Year: 2006).

Chan et al. "Design of Effective Zeolite Catalysts for the Complete Hydrogenation of $CO^{2}$" J. Am. Chem Soc. 2006, 128, 5322-5323.

REACTOR AND PROCESS FOR THE HYDROGENATION OF CARBON DIOXIDE

RELATED APPLICATIONS

This application is Divisional Application claiming priority to co-pending U.S. application Ser. No. 16/963,545, filed on Jul. 21, 2020, which is a National Stage Application under 35 U.S.C. 371 of expired PCT application PCT/NL2019/050046 designating the United States and filed Jan. 28, 2019; which claims the benefit of EP Application Serial No. 18153753.1 and filed Jan. 26, 2018 each of which are hereby incorporated by reference in their entireties.

The invention is in the field of chemical reactors and chemical processes. In particular, the invention is directed to a reactor and a process for the hydrogenation of carbon dioxide into methanol and/or dimethyl ether.

The process of hydrogenating carbon dioxide into methanol and/or dimethyl ether (also referred to as DME) can i.a. be used to lower $CO_2$ concentration in the atmosphere. In addition, the process can also be used to further valorize biogas and to provide a broader applicability of said biogas. For instance, by separating biogas into $CO_2$ and methane, the methane can be reformed into hydrogen ($H_2$) and the obtained hydrogen can be allowed to react with the $CO_2$ to form methanol and/or DME. This concept is not limited to biogas since in principle any $CO_2$-containing gas can be valorized and provided with a broader applicability by hydrogenating the $CO_2$ therein.

The hydrogenation of $CO_2$ is believed to involve the following reactions:

$$CO_2+3H_2 \rightleftharpoons CH_3OH+H_2O \quad (I)$$

$$CO_2+H_2 \rightleftharpoons CO+H_2O \quad (II)$$

$$CO+2H_2 \rightleftharpoons CH_3OH \quad (III)$$

$$2CH_3OH \rightleftharpoons CH_3OCH_3+H_2O \quad (IV)$$

The reaction $CO_2$ to MeOH can proceed directly (equation I), or via the intermediate CO (equation II and III). Depending on the process parameters, the obtained MeOH can react further into DME (equation IV). As is apparent from equations I-IV, water is produced as a side product concomitantly with MeOH and/or DME. In addition, since these reactions (I-IV) are in equilibrium under the process conditions, full conversion to the products can in principle not be obtained under thermodynamic equilibrium conditions. Therefore, in order to maximize the conversion into methanol and/or DME, it is preferred that at least one of the reaction products which is formed in the reaction (i.e. water, methanol and/or DME) is removed from the reaction medium.

Examples of conventional methods for the removal of the reaction products include condensation in a recycle configuration, reactive adsorption of water, and in-situ water-consuming reaction. US 2004/064002 discloses water vapor permeation through a membrane to remove the water from a reaction of MeOH to DME. In WO2015/030578, a reactor and a process are described comprising two stages including a zone or stage wherein a liquid condensate of methanol and water is condensed. However, all these methods are associated with several drawbacks.

For instance, a recycle configuration results in a bulky process design with installation of separate equipment, piping and control, while the use of solid system for the adsorption or reactive-consumption of water pose challenging regeneration and handling, also making the overall process bulky and expensive. Furthermore, a solid adsorption system involves regeneration which leads to a discontinuous type of operation and higher temperatures are needed for regeneration. Although the use of water vapor permeation through a membrane is elegant, this conventional method is associated with concomitant removal of $H_2$ from the reaction and decrease of the overall conversion. The combined condensation of methanol and water as disclosed in WO2015/0305578 requires a subsequent separation of the water and methanol in order to obtain dry methanol and results in a liquid methanol product, whereas it may be preferred to maintain a gaseous methanol product if is going to sequentially be converted into products in a gaseous phase reaction. This process is therefore relative high in energy consumption.

It is an object of the present invention to provide a process and reactor, in particular for the hydrogenation of carbon dioxide, that addresses at least one of these drawbacks.

A further object of the present invention is to provide an improved hydrogenation of carbon dioxide, by enhancing reaction rates towards the production of methanol and/or DME, improving catalyst lifetime, improving reactor design and intensification of process of production of methanol and/or DME from several steps to single reaction-separation-removal unit, and/or by providing a conversion beyond equilibrium constraints due to selective removal of at least one reaction product from the reaction mixture.

The present inventors found that these objects can at least partially be met by a combination of permeation of the formed water through a membrane and condensation of said water after permeation. This provides a method to selectively remove the water from the process, without the requirement of bulky process design with installation of separate equipment. The permeation and condensation are carried out in the same reactor, which reactor is another aspect of the present invention (vide infra). In particular, this method enables the in-situ removal of condensed water from the reaction within the same reactor in which the hydrogenation reaction is carried out.

Accordingly, the present invention is directed to a process for the hydrogenation of carbon dioxide, wherein said process comprises reacting carbon dioxide with hydrogen to form methanol and/or dimethyl ether, and water as a side product, and wherein said process further comprises removing said water from the process by a combination of permeation of said water through a membrane and condensation of the water.

In another aspect, the present invention is directed to a membrane reactor for the hydrogenation of carbon dioxide, said membrane reactor comprising a reaction compartment comprising a catalyst bed, a permeate compartment, and a water-permeable membrane that separates the reaction compartment and the permeate compartment. Said permeate compartment comprises a condensing surface such that the reactor is particularly suitable for carrying out the method of the present invention. The condensing surface in the permeate compartment is configured and is connected to a means for cooling (herein also referred to as cooling means) such that during operation of the reactor, the water can condense on the surface.

The means for cooling may be such to effect active and/or passive cooling. Examples of passive cooling include heat sinks and heat conductive materials that can be passively cooled by conductive cooling due to a temperature difference. Active cooling however is typically more effective and therefore preferred. Active cooling can be obtained by providing the means for cooling with an active-cooling device, for instance a passage such as a tube through which a cooling fluid can flow and/or a fan directing air. Suitable cooling fluids include gases (e.g. air) and liquids (e.g. water). A combination of active and passive cooling, e.g. by providing both fluid cooling through a tube or by a fan and a heat sink can also be used.

The water-permeable membrane is typically not exclusively permeable for water. For instance, hydrogen molecules, which are also present in the reaction compartment, are smaller than water molecules and may also (albeit undesirably) permeate the membrane. In fact, due to this permeation of hydrogen, substantial amounts of hydrogen removal from the reaction mixture have been observed in the aforementioned conventional methods. It is believed that the requirement of a sweeping gas stream to remove the vapor, also removes the permeated hydrogen. Advantageously, the presence of the condensing surface mitigates the requirement of the sweeping gas stream and the condensing surface selectively condensates water while hydrogen remains gaseous under the condensation and reaction conditions. With this method, separation of water from the reaction mixture and from $H_2$, may be carried out in one step, limiting the need of additional equipment for individual steps of separation and purification.

Typical reaction conditions include elevated temperatures and pressures. In particular, reacting carbon dioxide with hydrogen may be carried out at a temperature in the range of 150-400° C., preferably in the range of 200 to 300° C., more preferably about 250° C. and/or at a pressure in the range of 1-10 MPa, preferably in the range of 2-8 MPa, more preferably about 5 MPa.

The water-permeable membrane (herein also referred to as the membrane) can accordingly suitably function at these reaction conditions.

Therefore, the water-permeable membrane is preferably a hydrophilic membrane, which preferably comprises a zeolite membrane, an amorphous membrane or a polymer membrane. Particularly suitable zeolite membranes comprise mordenite (MOR), ZSM-5, chabazite (CHA), silicalite-1 (SIL-1), Z4A, faujasite (FAU), Si/Al variant MFI, and the like. Suitable amorphous membranes may comprise $Al_2O_3$/$SiO_2$. The polymer membranes may comprise ceramic-supported polymers (CSP), as these are particularly suitable for functioning at elevated temperatures. Membranes that are used for the water removal in Fischer-Tropsch processes may also be suitably used for the present invention (see e.g. Rohde et al. Microporous and Mesoporous Materials 115 (2008) 123-136).

The catalyst bed may comprise any known catalyst that suitably catalyzes the hydrogenation of carbon dioxide (see e.g. Gallucci et al. Chemical Engineering and Processing 43 (2004) 1029-1036 and references therein, which are incorporated herein in their entirety). Particularly suitable catalysts comprise copper, zinc oxide, zirconia, palladium, cerium(IV) oxide or combinations thereof. The catalyst may be supported on suitable supports such as alumina or silica. Advantageously, the present invention can increase the lifetime of the catalyst due to an increased removal of the water. As such, less water may condense in the catalyst particles, which can increase both performance and lifetime.

In FIG. 1, a particular embodiment of the reactor in accordance with the present invention is illustrated. The reactor comprises:

- an inner wall (5) bounding an inner space that defines the reaction compartment (2);
- an outer wall (7) that is arranged around said inner wall, wherein said outer wall (7) and inner wall (5) bound an outer space that defines the permeate compartment (4);
- wherein said inner wall (5) comprises the water-permeable membrane (51).

Preferably, as illustrated in FIG. 1, the inner wall and outer wall are tubular and the outer wall is co-axially arranged around said inner wall.

Figure 2:
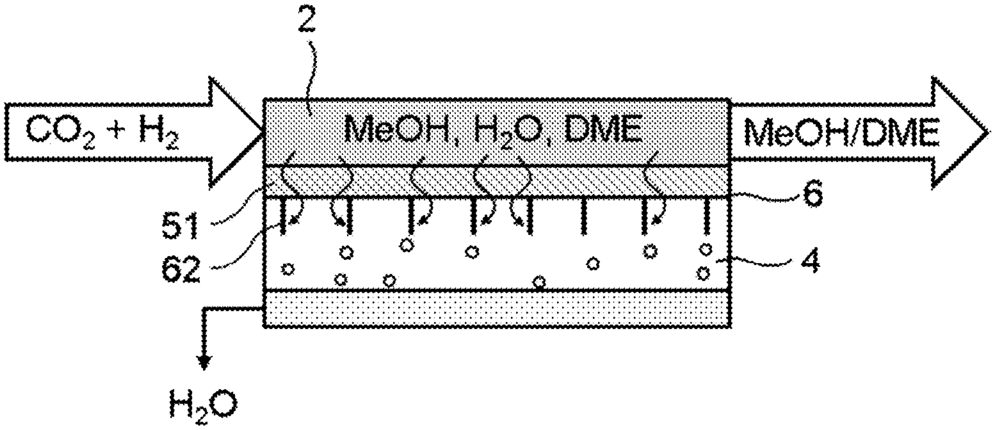

In a preferred embodiment, the condensing surface is part of a protruding surface elements (62) that are connected to or part of the cooling means. In a particular embodiment, the protruding surface elements are connected to said inner wall (5) and protruding into the permeate compartment. An example of this embodiment is illustrated in FIG. 2. In an alternative, embodiment, the protruding surface is connected to outer wall (7) and protruding into the permeate compartment (not shown). This may be preferred as condensation of water in the membrane is preferably prevented because condensed water in the membrane can block the membrane' pores. The protruding surface elements and thus the surface can have various shapes. For instance, the surface may be undulating or jagged to increase the total surface area. Suitable shapes may result from protruding elements such as rods, bars, blades and the like. Such protruding elements may comprise at least part of the active-cooling device such a tubing.

In particular embodiments, the condensing surface is situated in the reactor in the vicinity of the membrane. As such, the permeated water can travel a relatively short path before it condenses. The inventors found however, that in certain embodiments, it may actually be preferred that the cooling means and the condensing surface is situated in the reactor away from the membrane. For the hydrogenation reaction, typical reaction temperatures are around 250° C. due to which the membrane may have a temperature of about 200° C., while it is preferred that the condensing surface is kept at a much lower temperature (vide infra). Accordingly, such a temperature difference can more easily and efficiently be maintained when the cooling means and condensing surface are situated away from the membrane, or at least by situating the cooling means and condensing surface disconnected from the membrane and the inner wall. In addition, it can preferred condensed water in the membrane's pores. Away from the inner wall and in the vicinity of the outer wall herein means that the cooling means are closes to the outer wall than to the inner wall.

Figure 3:
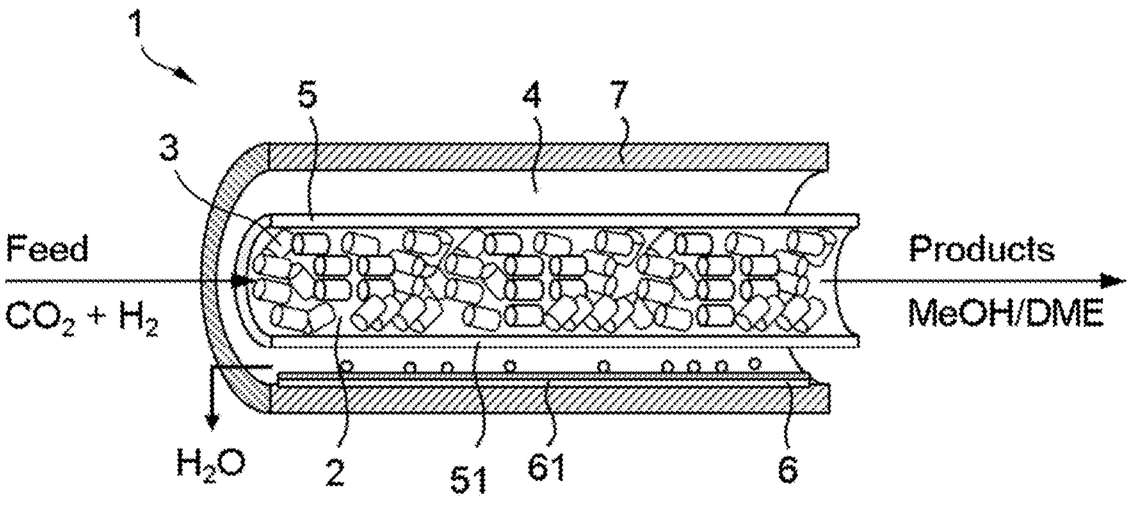

In FIG. 3, an embodiment of the reactor is shown, wherein the configuration is similar to that as illustrated in FIG. 1, but the means for cooling (6) in this embodiment is situated away from the inner wall (5) and more in the vicinity of the outer wall (7).

Figure 4:
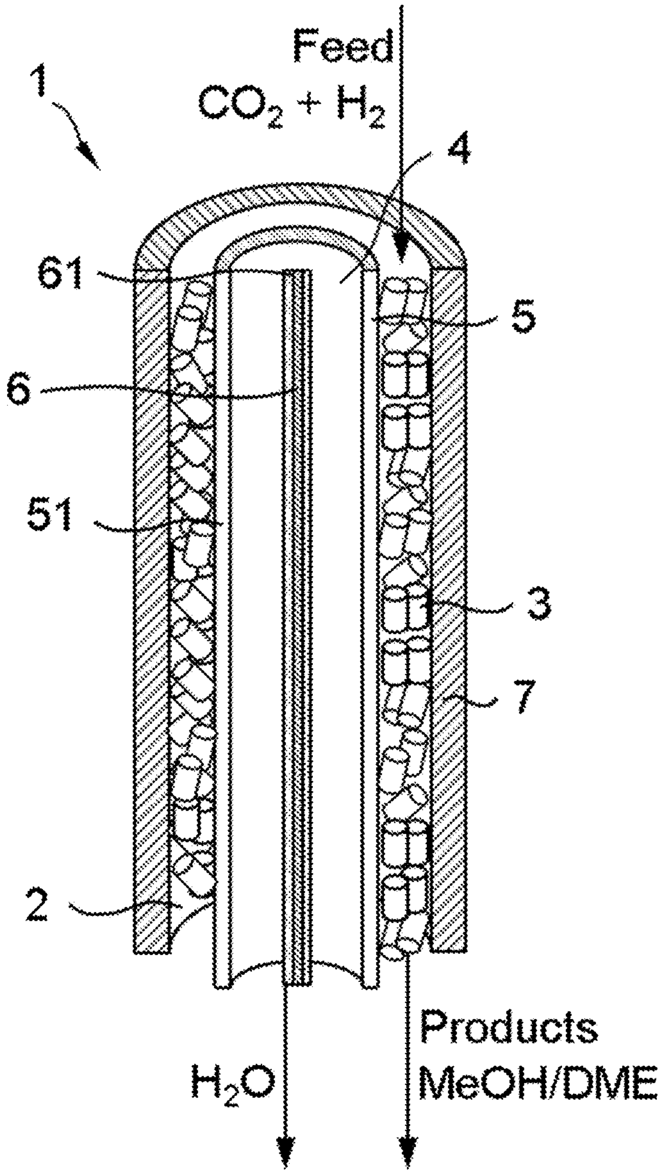

In FIG. 4, yet another configuration of the membrane reactor is illustrated. In this particular embodiment, which is preferred, the membrane reactor (1) comprises

- an inner wall (5) bounding an inner space that defines the permeate compartment (4);
- an outer wall (7) that is arranged around said inner wall, wherein said outer wall (7) and inner wall (5) bound an outer space that defines the reaction compartment (2);
  - wherein said inner wall (5) comprises the water-permeable membrane (51). Thus, the embodiment wherein the permeate compartment is at least partially enclosed by reaction compartment, is an inverse configuration of the reactor illustrated in FIGS. 1 and 3 wherein the reactor compartment is at least partially enclosed by the permeate compartment. As further illustrated in FIG. 4, preferably the cooling means (6) and the condensing surface (61) are located away from the inner wall. For instance, in an co-axial, tubular configuration of the reactor, the cooling means can be placed in the (longitudinal) axis of the reactor, as illustrated in FIG. 4 as well. The cooling means however, can have various shapes, and are not confined to a straight configuration as illustrated in FIG. 4. For instance, the cooling means can be a U-shaped, helical shaped, jagged and/or undulated tube, a various thereof. The cooling means can also comprise the protruding elements such as rods, bars, blades and the like.

The condensing surface is generally preferably actively cooled, meaning that it is maintained at a temperature by which water can condensate under the, generally elevated, reaction pressures. The condensing surface can be cooled actively by providing a cooling fluid stream, for instance air or (relatively) cool water, within tubing or a space near the condensing surface. It is to be understood that the cooling fluid should preferably be prevented from contacting the reactants in the reactor, such a hydrogen. The cooling fluid therefore is typically separated from the reaction compartment and the permeate compartment by a wall. For effective condensation under the reaction conditions, the condensing surface is preferably maintained at a temperature in the range of 50 to 150° C. The inventors however found that water can particularly effectively be condensed at less than 100° C., preferably less than 50° C.

Figure 10:
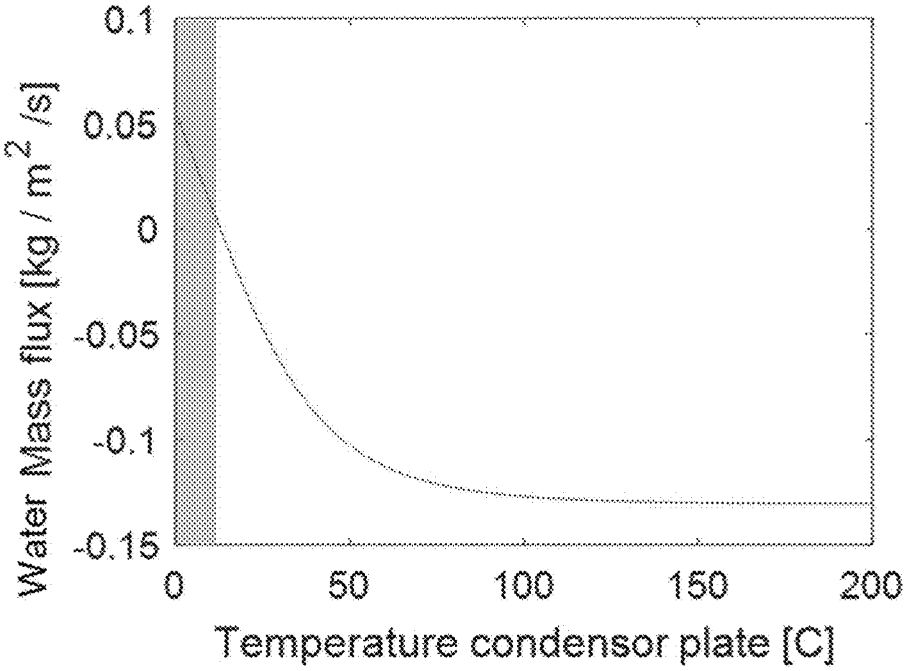

Surprisingly, the inventors found that in case the condensing surface is 10° C. or less, condensation of the water occurs in such an effective manner, that a water mass flux across the membrane can be achieved (see FIG. 10). The water mass flux across the membrane results in even better DME yields. For this reason, it is preferred that the cooling means of the reactor described herein, are adapted to be able to cool, preferably actively cool, the condensing surface to a temperature of less then 100° C., preferably less than 50° C., most preferably less than 10° C., during operation of the reactor wherein a reaction is carried out at a temperature in the range of 150-400° C., preferably in the range of 200 to 300° C., more preferably about 250° C.

The condensed water can be collected and let out the permeate compartment.

For the purpose of clarity and a concise description features are described herein as part of the same or separate embodiments, however, it will be appreciated that the scope of the invention may include embodiments having combinations of all or some of the features described.

The invention can be illustrated by the following non-limiting examples.

EXAMPLE 1—EFFECT OF WATER REMOVAL ON DME PRODUCTION

Figure 5:
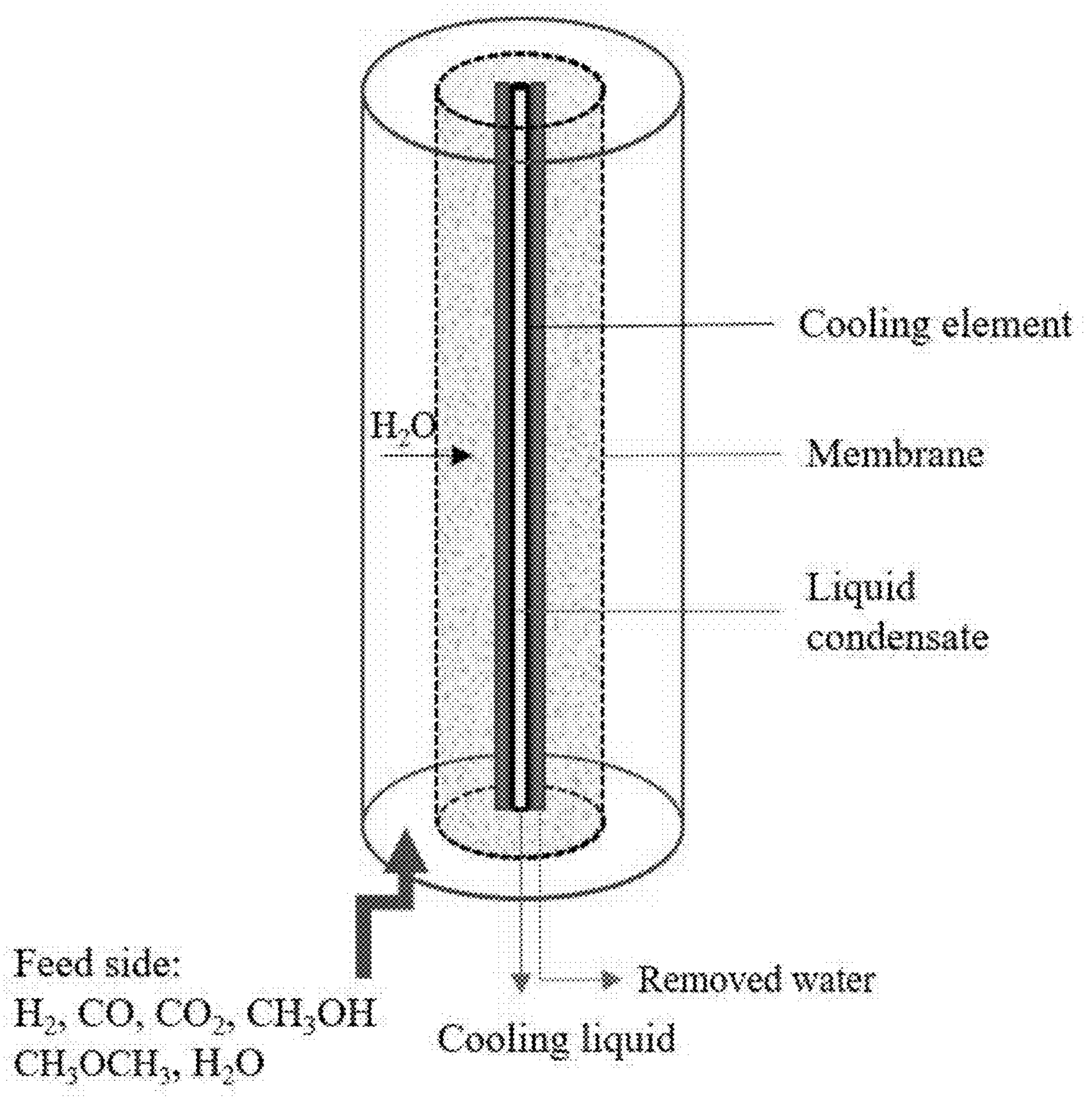

The following reaction and reactor is analysed in silico. In a membrane reactor as illustrated in FIG. 5, at the feed side (i.e. in the reaction compartment) a carbon dioxide hydrogenation reaction takes place to produce methanol and subsequent conversion to dimethyl ether, at 250° C. and 50 bar, according to the reactions 1-4. Reaction 3 is the combination of reaction 1 and 2. By removing water from reaction 4, the reaction can be shifted to the right-hand side to produce more dimethyl ether. Therefore, in-situ removal of water from the mixture of $H_2$, $H_2O$, CO, $CH_3OH$, $CH_3OCH_3$ will drive the reactions towards more DME production. To show the effect of water removal, two models were created.

$$CO+2H_2 \leftrightarrow CH_3OH \quad (1)$$

$$CO_2+H_2 \leftrightarrow CO+H_2O \quad (2)$$

$$CO_2+3H_2 \leftrightarrow CH_3OH+H_2O \quad (3)$$

$$2CH_3OH \leftrightarrow CH_3OCH_3+H_2O \quad (4)$$

In the first model kinetic equations and equilibrium constants for reaction 1-3 were used from Portha et al., Erena et al. and Alharbi et al., to show the establishment of chemical equilibrium in DME production. (see also Portha et al., *Ind. Eng. Chem. Res.,* 56 (2017) 13133-13145, Erena et al., *Chem. Eng. J.* 174 (2011) 660-667 and Alharbi et al. *ACS Catal* 5 (2015) 7186-7193. This equilibrium limits the amount of DME produced. By modelling the chemical equilibrium with and without water removal, it is shown that in-situ water removal with membrane reactor leads to an increase in DME production. Table 1 contains the starting conditions and pressures for the equilibrium model.

TABLE 1

Input values for equilibrium model

| Input values: | |
|---|---|
| T [° C.] | 250 |
| P [bar] | 50 |
| Start pressure $CO_2$ [bar] | 7.5 |
| Start pressure CO [bar] | 7.5 |
| Start pressure $H_2$ [bar] | 35 |

Figure 6:
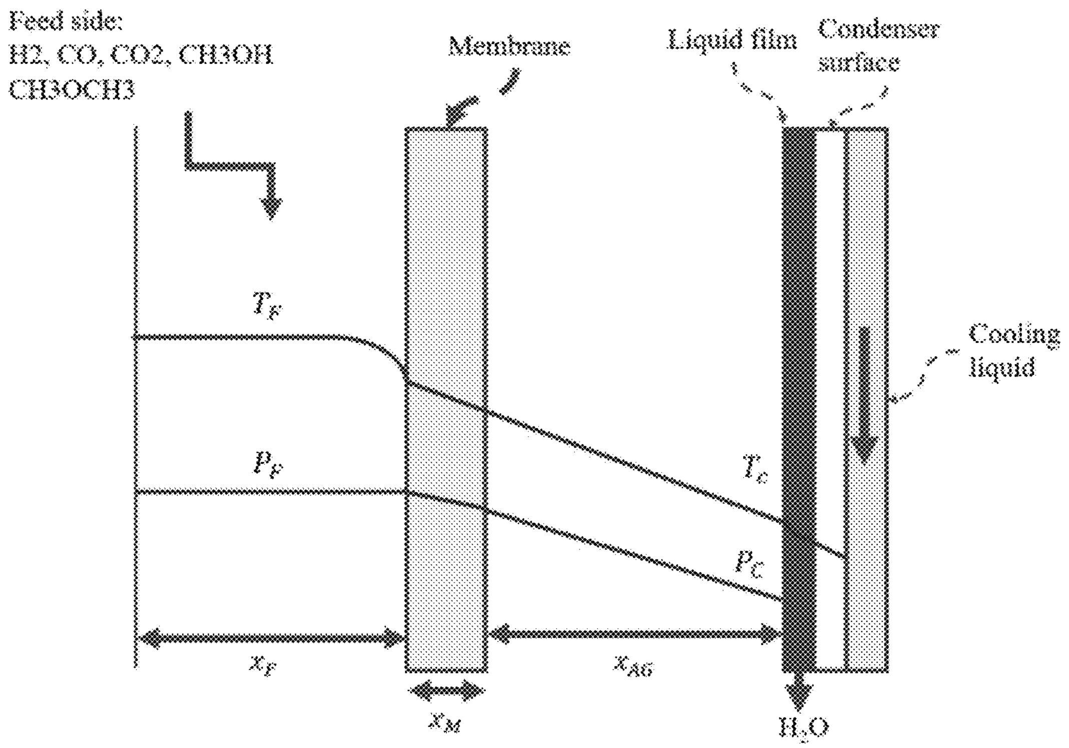

A second model calculates the steady state water removal by the membrane reactor, driven by the pressure difference between feed and permeate side. The calculated water removal from the feed side is used as an input for the first model in the graph, to show the increase in DME production. Additionally, variations in air gap and temperature of the cooling element show the effect of different parameter on the membrane reactor's performance For modelling a steady state in-situ water removal during conversion from $CO_2$ to dimethyl ether (DME), theory was used that is commonly applied for air gap membrane distillation processes used in water treatment. FIG. 6 shows the temperature and pressure profiles for the membrane reactor from FIG. 5. Water removal through the membrane is driven by a pressure difference between the water gas pressure on the feed side $P_F$ and the water pressure just above the liquid film on the condenser surface $P_C$.

The water gas pressure on the feed side is calculated by multiplying its calculated vapor fraction with the total pressure on the feed side of the reaction.

$$P_F=y_i*P_{total} \quad (5)$$

On the other side of the membrane, the vapor pressure just above the liquid film on the condenser surface is described by the Antoine equation (see equation 6).

$$P_C = 10^{4.6543-\frac{1435.264}{T_{cool}-64.848}}(1.0E+5) \quad (6)$$

The dominant mechanism for the water vapor mass flux is indicated by the Knudsen number. Equation 7 is used to calculate the Knudsen number, with $k_B$,T,r, $d_{H2O}$ and P as Boltzmann constant, temperature, membrane thickness, diameter water molecule and pressure.

$$K_n = \frac{k_B T}{2L\pi d_{H2O}^2 P\sqrt{2}} \quad (7)$$

A membrane thickness of 1 mm gives a Knudsen number smaller than 0.01 indicating that molecular diffusion through the air gap will be the mass transfer limiting step at 250° C. and 50 bar. Molecular diffusion through the air gap is usually the limitation in mass transfer in air gap membrane distillation.

Equation 8 gives the water flux for transition flow. Based on membrane properties in Table 2, a flux of 0.097 kg/m$^2$/s was calculated.

$$J = \frac{\varepsilon PDM\Delta p}{(\tau\delta + b)RT(P_a)} \quad (8)$$

TABLE 2 properties used in flux calculations

| Properties | Values used in calculation |
|---|---|
| Temperature condenser surface [° C. ] | 8 |
| Radius condenser element [mm] | 1 |
| Air gap [mm] | 2 |
| Vapor fraction $H_2O$ in feed gases yi | 2.94E−4 |
| Length membrane [m] | 0.1 |
| Membrane thickness [mm] | 1 |
| Membrane pore radius r [μm] | 1 |
| Porosity ε | 0.56 |
| Tortuosity τ | 2 |
| Diffusion coefficient water-air [m$^2$/s] | 2.8E−5 |
| Flow rate $H_2O$ feed side [1/s] | 3 |

Equation 8 represents the one-dimensional flux, whereas the experimental setup is cylindrical. As a simplification, the surface of the cylindrical membrane area was multiplied with the one-dimensional flux to get the total flux to be deposited on the inner cylindrical cooling element.

Figure 7:
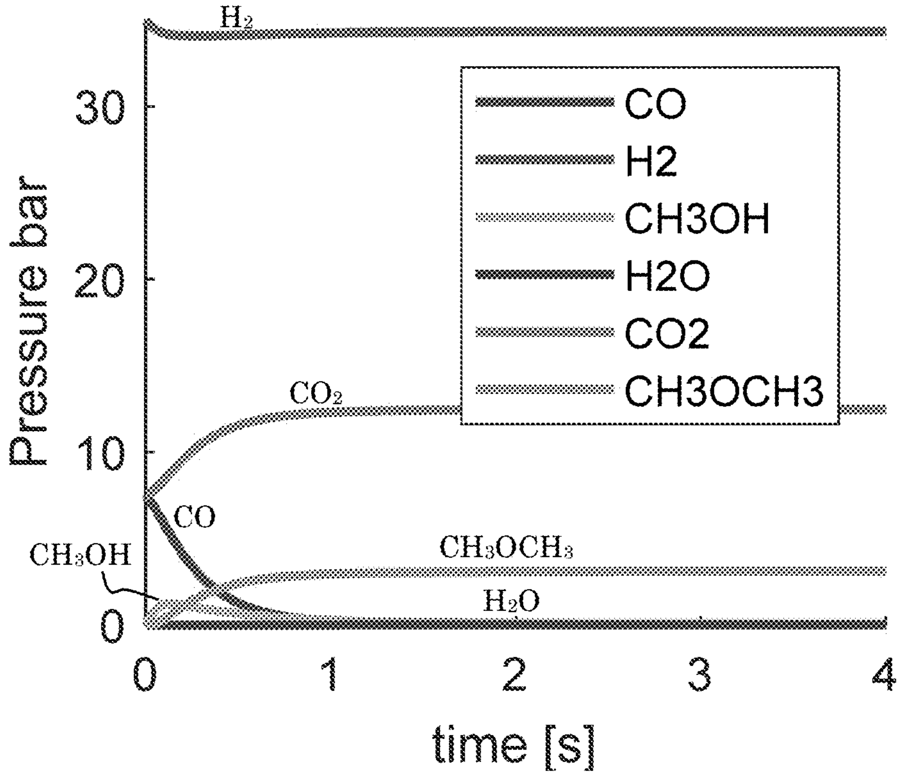
Figure 8:
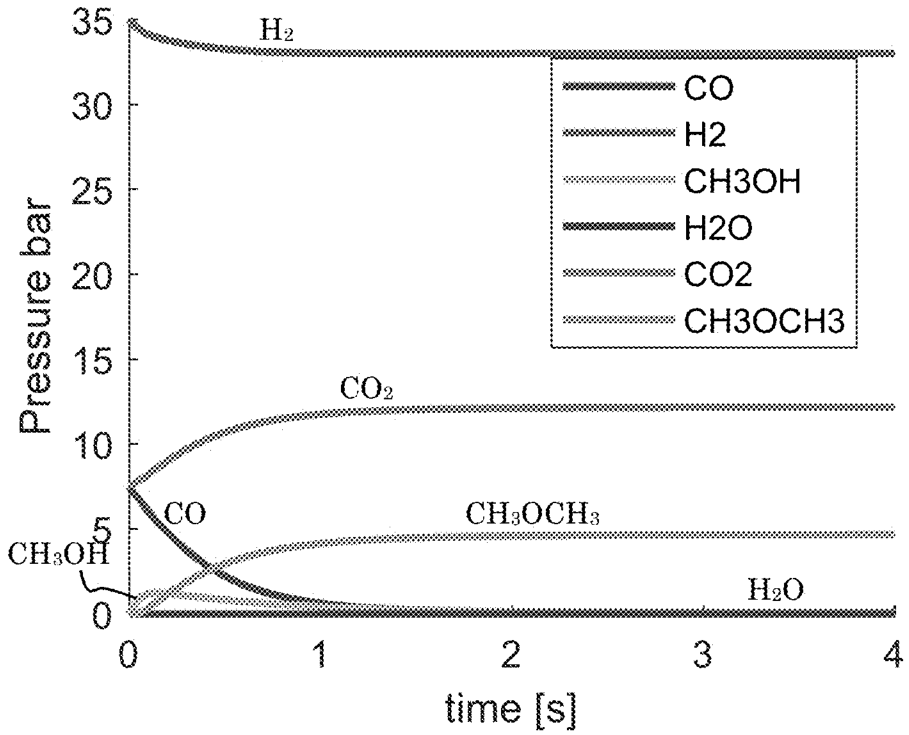
Figure 9:
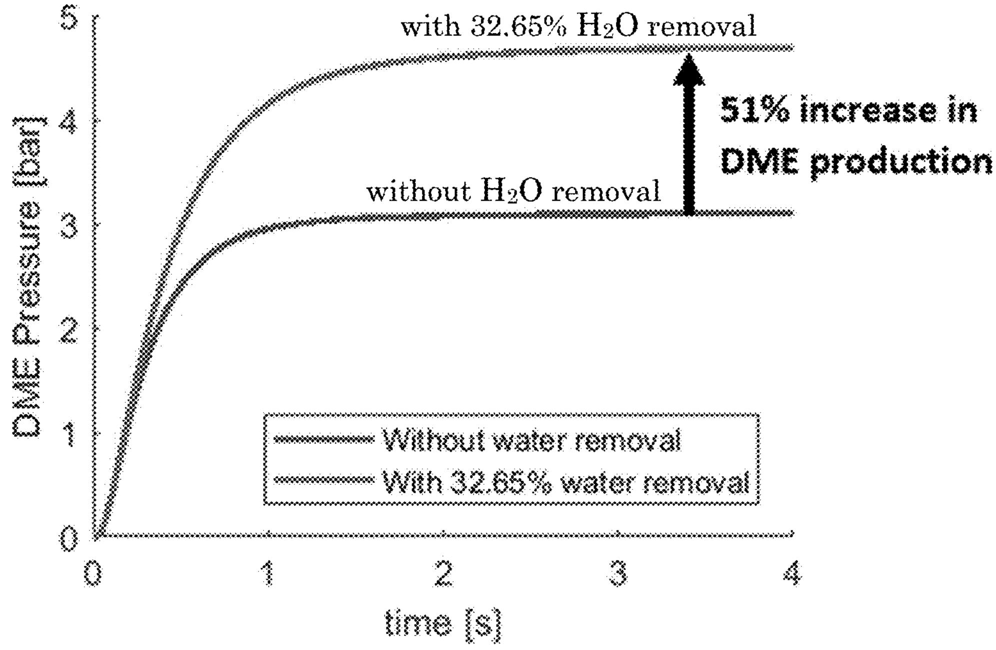

The result of the in silico reaction are illustrated in FIGS. 7 to 9.

FIG. 7 shows the model for establishing chemical equilibrium for reactions 1-4. This represents the chemical reactions that occur on the feed side of the membrane reactor, without water removal, starting from the pressures in Table 1. This can be compared to the situation where the cooling element at the permeate side of the membrane reactor is at the same temperature as the feed side and there is no in-situ water removal. Water is produced in reaction 3, but consumed in the water gas shift reaction (reaction 2 to the left hand side). Overall, without water removal, the end concentration of DME is 6.21 vol %.

FIG. 8 shows the same chemical equilibrium model with a constant water removal where 33% of the created water is removed. This amount of water removal matches with the water flux calculated in the model of the in-situ water removal membrane reactor with the standard parameters in Table 2. An equilibrium model with an added constant water removal corresponds to the situation where the reactions 2 and 3 shift more to the right-hand side of the equations due to the water removal, giving a higher DME yield. With water removal matching to the flux of water removal calculated in the membrane reactor model, the yield of DME rises with 51 vol %. FIG. 9 shows the 51 vol % increase in DME yield due to water removal.

EXAMPLE 2—EFFECT OF CONDENSING SURFACE TEMPERATURE ON THE FLUX OF WATER ACROSS THE MEMBRANE

Based on the models described in Example 1, the water mass flux over the membrane can be calculated, depending on the temperature of the condensing surface. The results are depicted in FIG. 10, from which it can be deduced that at condensing surface temperatures of >50° C., essentially no water flux is expected. The operating temperatures of membrane is close to 200° C. at which the condensation on/inside the membranes is not taking place. The results further show that active cooling with condensing temperature of <10° C. results in positive flux for water flux across the membrane.

The invention claimed is:

1. A process for the production of CO, methanol and/or dimethyl ether by hydrogenation of carbon dioxide carried out in a membrane reactor, wherein the membrane reactor comprises an inner wall and an outer wall that are tubular and wherein the outer wall is at least partially co-axially arranged around said inner wall;

a reaction compartment comprising a catalyst bed;

a permeate compartment; and a water-permeable membrane separating the reaction compartment and the permeate compartment, wherein said permeate compartment comprises:

a condensing surface; and a means for cooling that is connected to said condensing surface and wherein the cooling means and condensing surface are disconnected from the membrane and inner wall;

and wherein said process comprises:

leading hydrogen and carbon dioxide in the reaction compartment and reacting carbon dioxide with hydrogen to form CO, methanol and/or dimethyl ether, and water as a side product, and wherein said process further comprises removing said water from the process by a combination of permeation of said water through the water-permeable membrane and condensation of the water;

wherein said water is condensed at the condensing surface by cooling.

2. The process in accordance with claim 1, wherein the means for cooling comprises a passage through which a cooling fluid can flow.

3. The process in accordance with claim 1, wherein said reactor comprises an inner wall bounding an inner space that defines the reaction compartment;

an outer wall that is arranged around said inner wall, wherein said outer wall and inner wall bound an outer space that defines the permeate compartment;

wherein said inner wall comprises the water-permeable membrane, and wherein said condensing surface is connected to the outer wall.

4. The process in accordance with claim 1, wherein said reactor comprises an inner wall bounding an inner space that defines the permeate compartment;

an outer wall that is arranged around said inner wall, wherein said outer wall and inner wall bound an outer space that defines the reaction compartment;

wherein said inner wall comprises the water-permeable membrane, and wherein the condensing surface is located away from the inner wall.

5. The process in accordance with claim 1, wherein said means for cooling comprises a passage through which a cooling fluid can flow.

6. The process in accordance with claim 1, wherein the condensing surface comprises protruding surface elements.

7. The process in accordance with claim 1, wherein said water-permeable membrane comprises a hydrophilic membrane.

8. The process in accordance with claim 1, wherein said catalyst bed comprises copper, zinc oxide, zirconia, palladium, or cerium (IV) oxide or combinations thereof.

9. The process in accordance with claim 1, wherein the condensing surface has a temperature of less than 150° C.

10. The process in accordance with claim 1, wherein reacting carbon dioxide with hydrogen is carried out at a temperature in the range of 150-400° C. and/or at a pressure in the range of 1-10 MPa.

11. The process in accordance with claim 1, wherein said carbon dioxide and/or said hydrogen originate from biogas.

* * * * *